United States Patent [19]

Groll et al.

[11] Patent Number: 4,970,050
[45] Date of Patent: Nov. 13, 1990

[54] METHOD OF PRODUCING A SINTERED DENTAL PROSTHESIS

[76] Inventors: Werner Groll, Gartenstrasse 5, Alzenau-Huerstein; Angela Klaus, Werkstoffpruefferin, Feldstrasse 9, Hanau; Thomas Lange, Gerauer Strasse 86 A, Frankfurt am Main, all of Fed. Rep. of Germany

[21] Appl. No.: 448,115

[22] Filed: Dec. 13, 1989

[51] Int. Cl.$^5$ .............................................. B22F 1/00
[52] U.S. Cl. .................................... 419/36; 419/40; 419/54; 419/57; 419/60
[58] Field of Search ............... 419/23, 36, 54, 40, 419/60, 57

[56] References Cited

U.S. PATENT DOCUMENTS 4,277,283  7/1981  Tobioka et al. ................. 75/238
4,689,197  8/1987  Froll et al. ...................... 419/23
4,742,861  5/1988  Shohen et al. ................... 419/27
4,859,412  8/1989  Groll et al. ..................... 419/23

Primary Examiner—Stephen J. Lechert, Jr.

[57] ABSTRACT

A method of producing a sintered, very high density dental prosthesis from a suspension containing noble-metal powder mixtures with bi or multimodal particle-size distribution and a mixing liquid. The suspension is molded to the desired shape and then the dental prosthesis is dried. The molded dental prosthesis is then heat-treated 5 to 45 minutes between 100° and 400° C., then heated with an average temperature elevation of 50 to 300 K./min. to 800° C. and then brought to the sintering temperature T at 20 to 200 K./min. The sintering temperature T is between $T_{solidus} - 200$) and $T_{solidus} - 70$), whereby $T_{solidus}$ is the solidus temperature of the sintered alloy. The cooling-down of the dental prosthesis takes place under a vacuum or a protective gas.

36 Claims, 1 Drawing Sheet

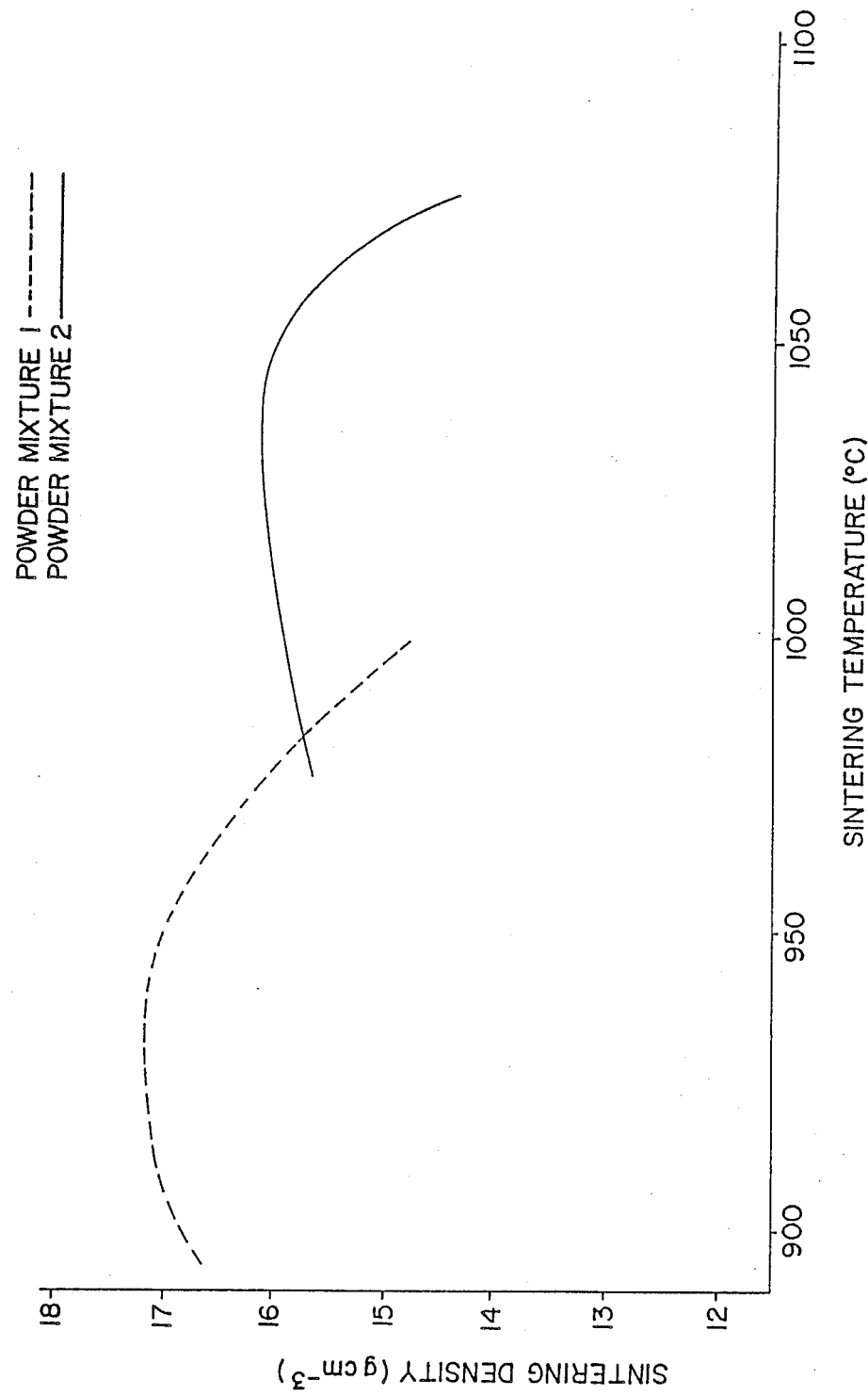

METHOD OF PRODUCING A SINTERED DENTAL PROSTHESIS

INTRODUCTION AND BACKGROUND

The invention relates to a method of producing a sintered dental prosthesis with a metallic structural matrix consisting of a noble-metal powder mixture or noble-metal alloy powder mixture with bi or multimodal particle size distribution and particles being primarily spherical in shape. The powder mixture is stirred with a mixing or conditioning liquid consisting basically of water to form a suspension capable of being modelled or molded as well as compressed so as to expel the mixing liquid. The dental prosthesis is formed by molding the suspension onto a model. The model functions as a firing carrier for the suspension molded onto the model through way of a technique customary in dental ceramics. The molded suspension is subsequently sintered onto the model in a graphite box or under a protective gas.

The production of a metallic dental prosthesis is often used for the prosthetic replacement following loss of teeth due to any one of the various dental diseases or after an accidental loss of one or more teeth. Examples of such prosthetic replacements include inlays, crowns and bridges which can be veneered with ceramics or plastic or which, when not veneered, can be cast with the so-called "wax-melt-out method", a casting technique which assures high dimensional accuracy.

The advantages of producing crowns and bridges with the "wax-melt-out method" include the aforementioned dimensional accuracy, high strength and a desirable degree of ductility, which must be assured in the case of rather large bridge constructions in order to avoid forced ruptures upon overloading. On the other hand, the method itself is very time-consuming, material-intensive and equipment-intensive. The necessity of using runners and casting cones causes a use of material which is distinctly elevated in relation to the weight of the cast object and which can result, in the case of repeated usage, in changes of the alloy properties and, if it is not reused, remains as scrap. Another disadvantage of this technique is the fact that in the case of errors in the cast object, a repair is not possible but rather the entire production process, starting with the wax modelling, must be repeated.

DE-OS No. 1 915 977 describes a method for the production of a metallic dental prosthesis using sintering technology in which the prosthesis is produced by applying to a model of the teeth a paste consisting of metal powder with a particle size between 2 and 25 $\mu$m and of a binder functioning as an adhesive and subsequently sintering the molded paste. One disadvantage of such a method resides in the poor compressibility of the described pastes, since the binder acting as adhesive cannot be expelled by compressing methods such as grooving or vibration. Moreover, since a powder fraction is used at the start, the density of the green compact is low, resulting in a great deal of shrinkage during sintering. Consequently, a high accuracy of fit is unobtainable which is not tolerable for most applications. The use of very fine powders between 2 and 25 $\mu$m does assure a very high sintering activity but entails high production costs in addition.

U.S. Pat. No. 4,661,071 discloses a method for the production of metallic dental prostheses using sintering technology and making use of powder having a size between 5–90 $\mu$m. The powder is made into a paste with a suitable binder and the metallic dental prosthesis is modelled on a model of the teeth to be provided. A special, castable and self-hardening edgeless mass is necessary for the production of the model which must be burned before the application of the metal powder at 1400° C.–1460° C.

Since traditional dental-ceramic firing-on kilns achieve maximum temperatures of up to approximately 1200° C., a special kiln is necessary for the process of U.S. Pat. No. 4,661,071. A liquid phase sintering process is used for sintering the metal powder under a vacuum of 1 HPa to $10^{-2}$ HPa. Since traditional dental-ceramic firing-on kilns does not achieve this vacuum, a special vacuum kiln is likewise necessary. Kilns with maximum temperatures of up to 1400° C. and kilns which assure a good vacuum at high temperatures are very much more expensive than normal ceramic firing-on kilns, so that the use of this method requires an expensive investment in equipment for a dental technician. Moreover, the use of the liquid phase sintering process results in problems in form stability during the sintering. In order to obtain as rapid a compression as possible by means of a rearrangement of the solid components, a liquid phase portion of at least 30–35% is necessary. (R. M. German, Liquid Phase Sintering, Plenum Press, N.Y., pp. 4,6,80). In analogy with the behavior of dental firing-on ceramics, a rounding or flattening of very delicate details, e.g. of an occlusal surface, must be reckoned with which can result in problems regarding the contact points and can possibly require considerable reworking.

DE-OS No. 35 32 331 describes a method for the production of metallic protheses using sintering technology which achieves a purposefully high density of the green compact using a powder mixture with multimodal size distribution. The powder mixture is converted with water into a suspension which is capable of being modeled and compressed. Accordingly, the shrinkage during sintering remains small. This is advantageous for the obtention of a good fit accuracy. The use of water as a mixing liquid to provide a consistency which is very similar to that of dental veneer ceramic suspensions permits an additional compression by means of expelling the liquid with the technology customary in dental ceramics (grooving, etc.). The sintering process can be carried out without very great expense in a traditional dental ceramic firing-on kiln. This can be achieved on the one hand by means of using a graphite box in which the modelled dental prosthesis to be sintered is located. This graphite box is placed in a customary dental ceramic firing-on kiln and assures a protection against the oxidation of base-metal components of the alloy at the sintering temperature. On the other hand, the introduction of protective gas into the ceramic firing-on kiln can likewise achieve a sufficient reduction of the partial oxygen pressure. After the sintering, the dental prosthesis is cooled off in the graphite box in air.

It proved to be disadvantageous in the above method, when using powder mixtures consisting of atomized, primarily spherical noble-metal alloys and precipitated, very fine, primarily spherical noble-metal powders, that maximum density values could not be achieved in the sintered state with the sintering parameters described in the method of DE-OS No. 35 32 331. This disadvantage is especially problematic in the case of multiple sintering as the density of the sintered prosthesis drops distinctly. However, multiple sintering can be necessary when producing bridges in several work steps or in the case of edge corrections.

SUMMARY OF THE INVENTION

The present invention is directed at solving the problems associated with the prior art by providing a method which does not require special tooling or specialized techniques and which helps to ensure an optimum density value in the sintered state, especially when multiple sintering is involved.

The solutions brought about by the present invention can be achieved by combining together, preferably by stirring, a mixing liquid formed primarily of water and a noble-metal powder mixture or noble-metal alloy powder mixture having multimodal particle size distribution and particles primarily spherical in shape. The combined material is stirred until a suspension is formed capable of being molded and compressed upon expulsion of the mixing liquid, onto a model of the teeth. The model of the teeth also functions as a firing carrier. The molded suspension is sintered onto the model in a graphite box or under a protective gas.

In carrying out the above process, the modelled and compressed dental prosthesis is first dried in air 5 to 25 minutes. The prosthesis is heat treated. Preferably the heat treatment involves placing the dental prosthesis into a graphite box and heat-treating the prosthesis for 5 to 45 minutes between 100° C. and 400° C. The heat is then raised to 800° C. with an average temperature elevation of 50 to 300 K/min. and is brought to the sintering temperature T above 800° C. with an average temperature elevation of 20 to 200 K/min. in air (in the graphite box) or under a protective gas. The sintering temperature T is between ($T_{solidus}$ - 200° C.) and ($T_{solidus}$ - 70° C.), whereby $T_{solidus}$ is the solidus temperature of the sintered alloy. The modelled dental prosthesis is sintered at this temperature 5 to 45 minutes in air (in the graphite box) or under protective gas and is then cooled off in a temperature range below 900° (e.g. between 900° C. and room temperature) under a protective gas or, when using a graphite box, also under a vacuum of 50 to 1 HPa. After cooling, the prosthesis can be removed from the graphite box.

The heating to sintering temperature and the sintering in the graphite box are preferably carried out in air and the cooling-off in a temperature range below 900° C. under a vacuum. This is particularly advantageous considering the use of the equipment normally present in a dental laboratory and considering the expense.

Preferred times for the heat treatment between 100° C. and 400° C. and the sintering are 5–25 minutes and 10–30 minutes, respectively.

If the work is not performed in a graphite box, it must be carried out under protective gas, in which instance the partial oxygen pressure should be less than $5 \times 10^{-2}$ HPa. This is assured, for example, if argon with industrial purity is used and can be realized by means of a relatively simple redesigning of a customary ceramics kiln.

A particular advantage of this method is the fact that a sufficiently high density coupled with closed porosity is achieved with the specified parameters, especially with the vacuum cooling, even after multiple sintering.

A mixture of primarily spherical powders with bi or multimodal distribution is used in the method of the invention. This powder mixture is mixed with a mixing liquid which consists primarily of water but can also contain slight additives of electrolytes such as, for example, strontium chloride, copper chloride or ammonium nitrate, mono or polyvalent alcohols, cellulose or polyethylene glycol to a suspension by hand mixing or with an agitator. The suspension is provided with consistency and modelling properties which correspond to those of customary dental and veneering ceramics.

The suspension prepared in this manner is applied with the technique customary in dental ceramics onto a highly temperature-resistant model of the teeth to be supplied and compressed there by means of known techniques (e.g. vibration with the grooved part of a modeling instrument, ultrasound, etc.). In utilizing such techniques, the liquid comes to the surface and is then removed with a cloth or dried in a current of warm air. It is recommended that the model's supporting surface be saturated or isolated with liquid before application of the suspension so that the model's supporting surface does not remove moisture from the suspension.

The green compact, compressed to a high gross density, is first allowed to stand in air on the model approximately 5–25 minutes so as to allow for slow drying. This can also take place on the cover plate of a ceramic firing-on kiln, which normally has a temperature $\leq 50°$ C. Then, the dental prosthesis located on the model is placed in a graphite box which completely surrounds it.

The prosthesis is then heat-treated in a kiln at a temperature between 100° and 400° C. for 5–45 minutes. This heat treatment serves to remove any moisture or organic contaminations still present. If this heat treatment is not performed before the actual sintering, fissures will form in the crown walls. If the temperature of 400° C. is exceeded and held for the times indicated, there is a drastic drop in the density of the sintered prosthesis.

After the heat treatment, the graphite box with the prosthesis located therein is heated to the sintering temperature. It is necessary for the attainment of a sufficiently high sintering density to bridge the temperature range between 400° C. and 800° C. with an average heating-up speed of more than 50 K/min., especially 50 to 300 K/min.

Lesser heating-up speeds result in a reduced density. Above 800° C. the average heating-up speed is selected with advantage to be between 20 and 200 K/min., which also results in justifiable times as regards the total sintering time.

The density of the sintered dental prosthesis is a function of the sintering temperature T. It has surprisingly turned out that the density exhibits a maximum in a temperature range between ($T_{solidus}$ - 200° C.) and ($T_{solidus}$ - 70° C.), whereby the exact position again depends on the special alloy. The maximum extends over a temperature range from 20°–50° C. and after the maximum has been exceeded, a very strong drop in the density values is observed. Two typical curves for two powder mixtures can be seen in FIG. 1.

The sintering of the dental prosthesis in the graphite box can be carried out in air or under protective gas. The sintering is preferably carried out in air since the results obtained are no worse than under protective gas and the cost of equipment is comparably less.

The sintering time is 5–45 minutes, whereby the maximum density is already attained as a rule at sintering times between 10 and 30 minutes.

A cooling-off of the sintered prosthesis in the graphite box in air results after the first sintering step in high densities. However, for the production of bridges or for a correction of occlusion, the contact points or of the edge closure, a second sintering step must, if necessary, be added. In spite of the same sintering cycle, the density of the prior art sintered prosthesis drops drastically when sintered twice.

It was surprisingly found that this drop in density in the case of multiple sintering can be prevented by cooling off the dental prosthesis located in the graphite box under a vacuum between 50 and 1 HPa. It is also advantageous if the vacuum required is present while the prosthesis is within the range of 900° C. to ambient temperature.

A sintering without a graphite box is also possible; however, the sintering must then take place under protective gas, in which instance the previously cited temperature and time data are just as valid. The partial oxygen pressure in protective gas should not exceed $5 \times 10^{-2}$ in order to achieve a sufficiently high density. The cooling-off should then likewise take place under protective gas.

DETAILED DESCRIPTION OF INVENTION

The following examples are intended to explain the method of the invention in more detail:

EXAMPLE 1

A suspension is formed into a consistency suitable for modelling by mixing powder mixture 1 (table 2, infra) with a mixing liquid consisting of 98% $H_2O$ and 2% polyethylene glycol. The suspension is applied with a brush onto a supporting stump saturated with liquid. The crown is completely modelled and the form checked repeatedly in an articulator.

The modelled suspension is compressed by grooving with the modelling instrument. The liquid exiting from the surface is removed with a cloth. The suspension is sufficiently cohesive to permit the construction of details of the occlusal surface such as elevations or grooves. After sufficient compression such that no more moisture exits from the surface, the surface can be reworked by scraping or cutting, so that even fine fissures can be created before the sintering. The crown, modelled to a finish, remains during the entire sintering process on a stump support. It is placed for drying onto the cover plate of a ceramic firing-on kiln and set after 15 minutes into a graphite box. The graphite box consists of a graphite bottom with an appropriate receptacle for the stump support and of a cup-shaped graphite cover. The graphite box with the modelled crown is placed into a kiln which is heated at the same time to 300° C. After 15 minutes, the graphite box is placed into a ceramic firing-on kiln preheated to 1000° C. and the temperature raised to 1050° C. The sintering temperature of 1050° C. is reached after 5 minutes, which corresponds to an average heating-up time of 150 K/min. The sintering temperature of 1050° C. is 160° C. below the $T_{solidus}$ temperature of 1210° C. (see table 2). After 20 minutes, the graphite box is removed from the kiln and cooled off in the air. A few minor corrections should be performed on the occlusal surface and edge areas. Then, the areas to be corrected are applied on the sintered crown as described above. Thereafter, the crown is resintered using the sintering cycle already described above. A check of the density yields a value of 14.2 g/cm³. The crown is too large because the cooling took place in air.

EXAMPLE 2

Another crown is produced in analogy with example 1. However, after termination of the sintering at 1050° C., the graphite box with the crown in moved into an evacuatable cooling chamber. The cooling chamber is evacuated to a vacuum of approximately 50 HPa immediately after the moving of the graphite box. The cooled-down specimen can be removed after approximately 15 minutes. As described in example 1, a few minor corrections are performed. The crown is resintered and cooled again under a vacuum. The stump support mass is blasted out using a sandblast machine and the density determined. It is now 16.1 g/cm³ and the porosity is closed. The crown is worked up and polished. The edge slot in the master model is on the average 40 μm.

EXAMPLE 3

Powder mixture 2 (table 2) is used for producing inlays because this alloy is yellow and is preferred by many patients. In addition, it exhibits a lesser permanent elongation limit and an elevated ductility. This makes it easier to finish the edges in the mouth. The production takes place analogously to the method described in example 2.

However, the sintering cycle is modified somewhat After the drying in air, the inlay located on the model stump (in graphite box) is placed onto the firing table of an open ceramic firing-on kiln preheated to 700° C. A temperature of approximately 250° C. prevails on the firing table. After 9 minutes the firing table automatically moves in and the kiln heats up to the sintering temperature of 940° C. After another 15 minutes, the specimen can be removed from the kiln, moved into the cooling-off chamber and cooled off there under a vacuum of 50 HPa. The stump mass is blasted out, the inlay worked up, set on the master model stump and polished. The density is 17.1 g/cm³, the porosity is closed. The polishing also closes the pores situated on the surface. The edge slot is approximately 50 μm. The temperature-change speed between 400° and 800° C. was on the average approximately 120 K/min. and, the temperature-change speed between 800° C. and the sintering temperature was on the average 100 K/min. $T_{solidus}$ = 1040° C. (table 2).

Palladium alloys can also be worked in the same manner.

Table 1 shows the composition of the alloys used in the examples, their production, grain form and grain size, whereas table 2 shows the composition of the powder mixtures used in the examples.

FIG. 1 represents the dependence of the sintering density of dental prosthesis parts on the sintering temperature in accordance with the powder mixtures contained in table 2.

The information contained in German Priority Application P 38 41 9022.5-24 is incorporated herein by reference.

TABLE 1

| | (Composition of Alloys) | | | |
|---|---|---|---|---|
| | Composition (portion of mass in %) | Grain form | Production | Grain size/μm |
| Alloy 1 | Au 65 Pt 15 Pd 13 | Primarily spherical | Atomization | —* |

TABLE 1-continued
(Composition of Alloys)

| | Composition (portion of mass in %) | Grain form | Production | Grain size/μm |
|---|---|---|---|---|
| Alloy 2 | In 2.5 + additives each <2% Au 87 Pt + additives each <2% | Primarily spherical | Atomization | —* |
| Au powder 1 | Au | Primary spherical | chem. precipitation | <5 |
| Au powder 2 | Au | Primarily spherical | chem. precipitation | <10 |

*depending on screening, always <100 um

TABLE 2
(Examples for Powders Used)

| | Component 1 Powder content KG**/μm % | Component 2 Powder content KG/μm % | Component 3 Powder content KG/μm % | $T_{solidus}$* |
|---|---|---|---|---|
| Powder mixture 1 | Alloy 1 80 <63 | Au 1 20 <5 | | 1210° C. |
| Powder mixture 2 | Alloy 2 85 <50 | Au 1 13 <5 | Au 2 2 <10 | 1040° C. |

*$T_{solidus}$ of the sintered alloy
**KG = grain size

What is claimed is:

1. A method for producing a sintered dental prosthesis, comprising:
    mixing a noble-metal or noble-metal alloy powder mixture with a mixing liquid to form a moldable suspension;
    molding said suspension onto a model;
    applying a drying treatment to said molded suspension;
    heat treating said molded suspension by subjecting said molded suspension to a heat treating medium at a temperature $T_1$ which is between 100° C. to 400° C.;
    raising the temperature of the heat treating medium to a higher temperature level $T_2$;
    sintering said molded suspension in a container by further raising the temperature of the heat treating medium to a sintering temperature $T_3$, with $T_3$ being between ($T_{solidus}$ 200° C.) and ($T_{solidus}$ - 70° C.), and with $T_{solidus}$ being the sintered temperature of the sintered powder mixture.

2. A method as recited in claim 1, further comprising cooling said molded suspension while maintaining a vacuum in the container.

3. A method as recited in claim 2, wherein the temperature increase from $T_2$ to $T_3$ is achieved at a temperature elevation of about 20 to 200 K/min.

4. A method as recited in claim 2, wherein the sintered molded suspension is cooled off in a temperature range below 900° C. under a vacuum of 50-1 HPa.

5. A method as recited in claim 2, wherein said molded suspension is subjected to temperature $T_1$ for a period of between about 5 to 45 minutes.

6. A method as recited in claim 5, wherein said molded suspension is sintered 5 to 45 minutes.

7. A method as recited in claim 2, wherein the sintering is carried out in air and the cooling of said molded suspension occurs in a vacuum temperature below 900° C.

8. A method as recited in claim 1, wherein said molded suspension is subject to temperature $T_1$ for a period between 5 to 25 minutes.

9. A method as recited in claim 8, wherein said molded suspension is sintered for 10 to 30 minutes.

10. A method as recited in claim 6, wherein $T_2$ is about 800° C. and the average temperature elevation rate from $T^1$ to $T^2$ is between about 50 K/min and 300 K/min.

11. A method as recited in claim 1, wherein the molded suspension is sintered for about 5 to 45 minutes.

12. A method as recited in claim 1, wherein said container is a graphite box.

13. A method as recited in claim 1, wherein $T_2$ is about 800° C.

14. A method as recited in claim 1, wherein said powder mixture has a bimodal to multimodal particle size distribution and comprises primarily spherical shaped particles.

15. A method as recited in claim 1, wherein the drying treatment of said molded suspension includes subjecting said suspension to air for 5 to 25 minutes.

16. A method as recited in claim 1, wherein the temperature increase from $T_1$ to $T_2$ is achieved at a temperature elevation of about 50 to 300 K/min.

17. A method as recited in claim 16, wherein the temperature increase from $T_2$ to $T_3$ is achieved at a temperature elevation of about 20 to 200 K/min.

18. A method as recited in claim 16, wherein the molded suspension is sintered at temperature $T_3$ in air for 5 to 25 minutes.

19. A method as recited in claim 16, wherein the molded suspension is sintered at temperature $T_3$ in air for 10 to 30 minutes.

20. A method of producing a sintered dental prosthesis, comprising:
    mixing a noble or noble-metal alloy powder mixture with a mixing liquid to form a moldable suspension;
    molding said suspension onto a model;
    drying said molded suspension by subjecting said molded suspension to a heat treating medium at a temperature $T_1$ which is about 100° C. to 400° C.;
    raising said temperature level of the heat treating medium to a higher temperature $T_2$;
    sintering said molded suspension under a protective gas which provides support in the prevention against oxidation of base-metal components in said powder mixture, said sintering being achieved by further raising the temperature of the heat treating medium to a sintering temperature $T_3$, with $T_3$ being between ($T_{solidus}$ - 200° C.) and ($T_{solidus}$ - 70° C.), and with $T_{solidus}$ being the sintered temperature of the sintered alloy.

21. A method as recited in claim 20, further comprising cooling said molded suspension under a protective gas.

22. A method as recited in claim 21, wherein the protective gas contains argon.

23. A method as recited in claim 20, wherein a partial oxygen pressure develops through utilization of said protective gas and the partial oxygen pressure is maintained at less than $5 \times 10^{-2}$ HPa during the raising of the temperature from $T_2$ to $T_3$, during the sintering step and during the cooling step.

24. A method as recited in claim 20, wherein the heat elevation rate from $T_1$ to $T_2$ falls within the averages of about 50 to 300 K/min.

25. A method as recited in 24, wherein the temperature elevation rate from $T_2$ to $T_3$ is a rate between about 20 to 200 K/min.

26. A method as recited in claim 20, wherein said molded suspension is subject to temperature $T_1$ for a period between 5 to 45 minutes.

27. A method as recited in claim 20, wherein said molded suspension is sintered 5 to 45 minutes.

28. A method as recited in claim 26, wherein $T_2$ is about 800° C.

29. A method as recited in claim 20, wherein said molded suspension is sintered for 10 to 30 minutes.

30. A method as recited in 20, wherein said molded suspension is subjected to temperature $T_1$ for a period between 5 to 25 minutes.

31. A method as recited in claim 20, wherein $T_2$ is about 800° C.

32. A method as recited in claim 20, wherein said powder mixture has a bimodal to multimodal particle size distribution and comprises primarily spherical shaped particles.

33. A method as recited in claim 20, wherein drying of said molded suspension includes subjecting said suspension to air for 5 to 25 minutes.

34. A method as recited in claim 33, wherein the molded suspension is sintered at temperature $T_3$ in air for 5 to 45 minutes.

35. A method as recited in claim 33, wherein the molded suspension is sintered at temperature $T_3$ in air for 10 to 30 minutes.

36. A method as recited in claim 20, wherein the temperature increase from $T_2$ to $T_3$ is achieved at a temperature elevation of about 20 to 200 K/min.

* * * * *